(12) United States Patent
Shelley et al.

(10) Patent No.: US 7,075,086 B2
(45) Date of Patent: Jul. 11, 2006

(54) MEASUREMENT OF METAL POLISH QUALITY

(75) Inventors: Paul H. Shelley, Lakewood, WA (US); Bruce R. Davis, Seattle, WA (US)

(73) Assignee: The Boeing Company, Chicago, IL (US)

( * ) Notice: Subject to any disclaimer, the term of this patent is extended or adjusted under 35 U.S.C. 154(b) by 198 days.

(21) Appl. No.: 10/653,014

(22) Filed: Aug. 28, 2003

(65) Prior Publication Data

US 2005/0045824 A1 Mar. 3, 2005

(51) Int. Cl.
*G01J 5/02* (2006.01)

(52) U.S. Cl. .............................. 250/341.8; 250/559.11; 250/559.39

(58) Field of Classification Search ............ 250/341.8, 250/559.11, 559.39, 339.01, 339.02, 339.03, 250/339.04, 339.05, 339.06, 339.07, 339.08, 250/339.09, 339.1, 339.11, 339.12, 339.13, 250/339.14, 339.15
See application file for complete search history.

(56) References Cited

U.S. PATENT DOCUMENTS

| | | | | |
|---|---|---|---|---|
| 2,215,211 A | * | 9/1940 | Devol | ........................ 356/447 |
| 2,254,062 A | * | 8/1941 | Devol | ........................ 356/446 |
| 3,017,512 A | | 1/1962 | Wolbert | |
| 3,693,025 A | | 9/1972 | Brunton | |
| 3,973,122 A | | 8/1976 | Goldberg | |
| 3,994,586 A | | 11/1976 | Sharkins et al. | |
| 4,284,356 A | * | 8/1981 | Heilman | ........................ 356/429 |
| 4,345,840 A | * | 8/1982 | Goetz et al. | ................. 356/407 |
| 4,549,079 A | | 10/1985 | Terasaka et al. | |
| 4,791,296 A | | 12/1988 | Carpio | |
| 4,800,279 A | | 1/1989 | Hieftje et al. | |
| 5,015,856 A | | 5/1991 | Gold | |
| 5,091,647 A | | 2/1992 | Carduner et al. | |
| 5,289,266 A | | 2/1994 | Shih et al. | |
| 5,358,333 A | | 10/1994 | Schmidt et al. | |
| 5,381,228 A | | 1/1995 | Brace | |
| 5,401,977 A | | 3/1995 | Schwarz | |
| 5,477,332 A | * | 12/1995 | Stone et al. | ................. 356/613 |
| 5,795,394 A | | 8/1998 | Belotserkovsky et al. | |
| 6,052,191 A | | 4/2000 | Brayden, Jr. et al. | |
| 6,074,287 A | * | 6/2000 | Miyaji et al. | ................ 451/287 |
| 6,184,528 B1 | | 2/2001 | DiMarzio et al. | |
| 6,794,560 B1 | * | 9/2004 | Harberd et al. | ............. 800/290 |
| 2003/0151747 A1 | * | 8/2003 | Nagarajan et al. | .......... 356/446 |
| 2004/0099807 A1 | | 5/2004 | Shelley et al. | |
| 2004/0217290 A1 | * | 11/2004 | Davis et al. | ............. 250/341.8 |
| 2004/0256564 A1 | * | 12/2004 | Allen et al. | ............ 250/339.11 |
| 2005/0006590 A1 | * | 1/2005 | Harrison | ..................... 250/372 |

FOREIGN PATENT DOCUMENTS

| | | |
|---|---|---|
| DE | 2252527 | 10/1972 |
| DE | 4344095 | 12/1993 |
| EP | 1 128 178 A1 | 8/2001 |
| EP | 1 233 261 A1 | 8/2002 |
| WO | WO 01/92820 A1 | 12/2001 |

\* cited by examiner

*Primary Examiner*—David Porta
*Assistant Examiner*—Christopher Webb
(74) *Attorney, Agent, or Firm*—Lee & Hayes, PLLC

(57) ABSTRACT

A value of infrared energy reflected from a metallic substrate with a polished surface is determined. The value of the infrared energy reflected, or conversely absorbed, is correlated to a quality of polish. According to an aspect of the invention, one embodiment of the invention utilizes an infrared spectrometer to determine the infrared absorbance of a polished metallic substrate. An infrared beam is reflected off the metallic substrate. The infrared energy of the reflected beam is compared with a pre-determined value of infrared energy reflected off a reference polish surface.

56 Claims, 5 Drawing Sheets

MEASUREMENT OF METAL POLISH QUALITY

FIELD OF THE INVENTION

This invention relates generally to measurement, and, more specifically, to measurement of metal surfaces.

BACKGROUND OF THE INVENTION

Bare metal surfaces are utilized in a variety of applications, such as the outer surfaces or skins of vehicles, including aircraft. Bare metal surfaces are polished for aesthetic and drag reduction purposes. Ascertaining the degree and quality of a metal polish has typically been performed by visual inspection, with the inspector relying on his or her experience and on reference samples containing various surface polishes. Thus, current visual polish inspections involve a substantial degree of subjectivity.

Panels manufactured and polished at different times, or by different processes or entities, may have different polish qualities and thus, look different from each other. Typically, clean polished metal surfaces present a uniform color when viewed from a position perpendicular to the surface, but often show variations in color or reflectivity when viewed from an angle if the degree of polish differs. In equipment where uniform polish is desired, such as with vehicles or fleets, uniformity of polish quality is important. By way of example, aircraft constructed with aluminum skin sections of differing degrees of polish can present an undesirable checkerboard or segmented look. In equipment manufactured in different segments, obtaining a uniform degree of polish across multiple segments may also be important. However, as previously stated, current visual inspection of polish for quality control and panel matching involves a substantial degree of subjective judgment by the visual inspector.

Therefore, there currently exists an unmet need in the art for a non-destructive, quantitative, and objective determination of quality of polishing on metal substrates.

SUMMARY OF THE INVENTION

The present invention provides a non-destructive method for efficiently and objectively determining the degree of polish on a metallic substrate or sample. The present invention may be used to measure the degree of polish over a wide area, and to quantitatively provide measurements of the degree of polish. Advantageously, the present invention provides an objective, quantitative method for measuring the degree of polish on metal substrates.

According to one embodiment of the present invention, a value of infrared energy reflected from a metallic substrate with a polished surface is determined. The value of the infrared energy reflected, or conversely absorbed, is correlated to a degree of polish. According to one aspect of the present invention, one method utilizes an infrared spectrometer to determine infrared absorbance of a polished metallic substrate. An infrared beam is reflected off the metallic substrate. The infrared energy of the reflected beam is then compared with the pre-determined value of infrared energy reflected off a reference polished surface to determine the degree of polish.

According to another aspect of the present invention, a ratio of infrared energy absorbance of at least two wavelengths of a polished metallic substrate is compared with a reference polished surface.

BRIEF DESCRIPTION OF THE DRAWINGS

The preferred and alternative embodiments of the present invention are described in detail below with reference to the following drawings.

DETAILED DESCRIPTION OF THE INVENTION

By way of overview, a non-destructive method is provided for determining a degree of polish of a metallic substrate. A value $I_s$ of infrared energy reflected by a polish surface on a metallic substrate is determined. The value $I_s$ of infrared energy reflected by the polish surface correlates to a degree of polish.

The degree or quality of polish corresponds to surface smoothness at a very fine scale of the metallic substrate. Higher quality polished surfaces are smoother, and reflect light more uniformly and with less scatter than lower quality polishes. Increasing degrees or qualities of polish are suitably obtained by increasing polishing time and by the use of progressively finer grained polishing compounds.

Figure 1:
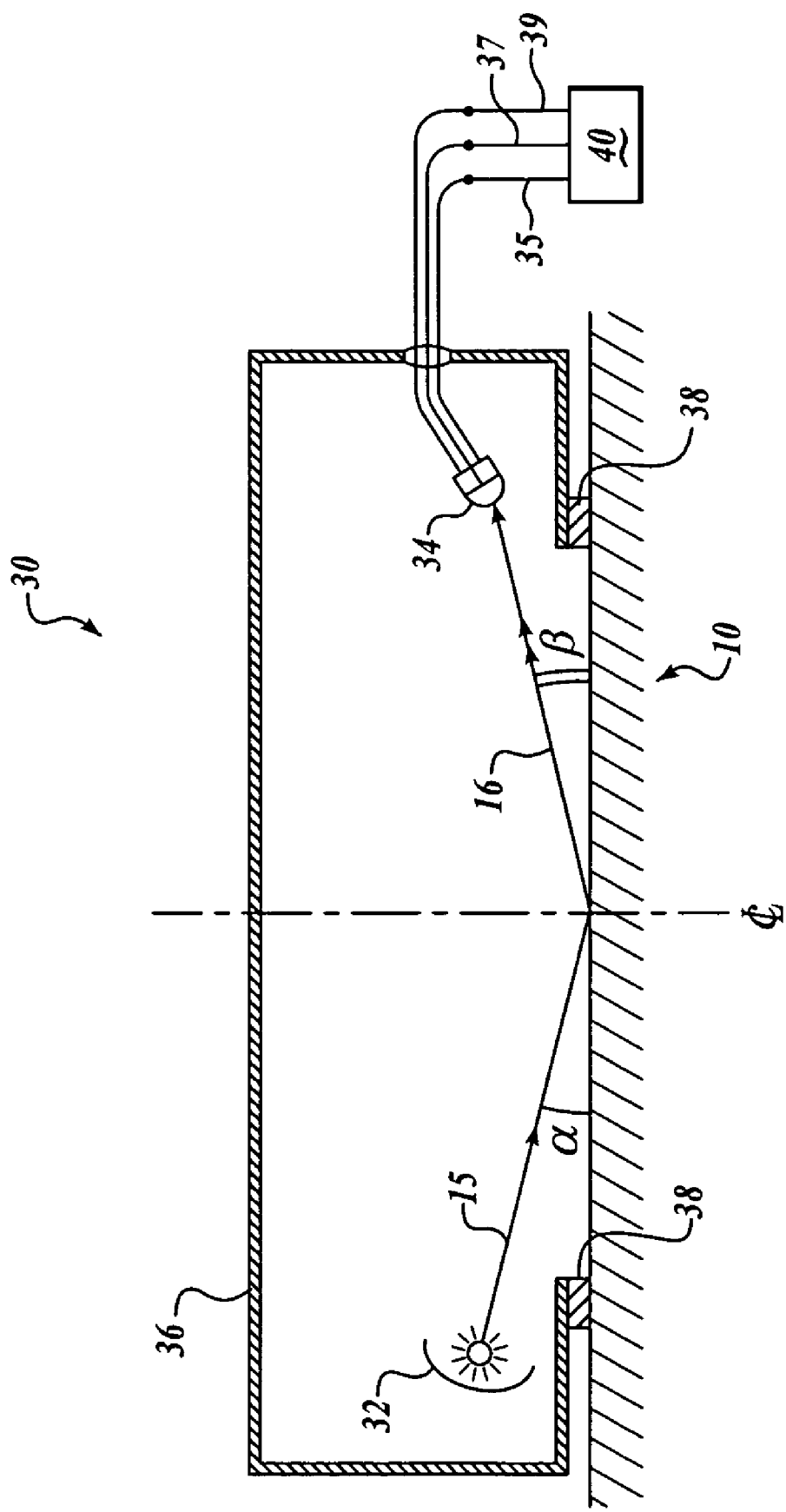
FIG. 1 is a cross-section drawing of a polish measurement device in accordance with the present invention.

FIG. 1 is a cross-section drawing of an exemplary testing device 30 used to determine the quality of polish on a metallic substrate according to one presently preferred embodiment of the invention. An infrared transmission beam 15 is transmitted by an infrared source 32. The beam 15 is reflected off a sample surface 10, and the reflected beam 16 is detected by an infrared detector 34. It will be appreciated that the infrared source 32 and the infrared detector 34 suitably may include an infrared spectrometer. The infrared source 32 suitably may include a multi-frequency infrared source 32, and the infrared detector 34 may include a single or multiple frequency detector. In the embodiment shown in FIG. 1, the infrared detector 34 detects infrared energy at two wavenumbers. The infrared levels received by the infrared detector 34 are output as an electrical signal to a processor or display 40 through a common conductor 37, a low frequency output conductor 35 and a high frequency output conductor 39.

The detector 34 may suitably detect infrared energy including the utilization of one or more narrow pass filters (not shown) and a broadband infrared source 32. In another presently preferred embodiment, the infrared source 32 and infrared detector 34 are suitably included in a portable infrared spectrometer such as a SOC-400 FTIR, manufactured by Surface Optics Corporation. In an alternate embodiment, an imaging infrared spectrometer may be utilized.

It will be appreciated that in this exemplary testing device 30, the infrared beam 15 has an angle of incidence α to the surface 10 of approximately 15 degrees. The reflected infrared beam 15 has an angle of reflection β of 15 degrees from the surface 10. It will be appreciated that the angle of incidence α may vary with materials being measured, so long as consistent angles of incidence α and reflectance β are utilized for comparing different samples.

The testing device 30 suitably measures a grazing infrared reflectivity of the surface 10. It will be appreciated that oblique reflection off the surface 10 is more sensitive to surface texture than acute reflection.

The testing device 30 includes a housing 36 holding the infrared source 32 and infrared detector 34. The housing 36 rests on feet 38 that hold the infrared source 32 and infrared detector 34 at a predetermined distance and position relative to the surface 10. The mobility of the device 30 permits additional measurements of adjoining areas and other samples with comparable results. It will be appreciated that the testing device 30 shown in FIG. 1 suitably measures grazing angle specular reflectance at an angle greater than 70 degrees from normal to the surface 10.

The device 30 of FIG. 1 may be utilized to non-destructively determine the degree of polish on the surface 10. Initially, a base reference value $I_o$ of infrared energy reflected by a reference polished metallic sample (not shown) is determined. The device 30 is then used to transmit the infrared beam 15 to the surface 10 to be tested. A comparison is made between the reflected infrared energy of the sample and the reflected infrared energy reference to calculate a quality of polish.

Figure 2:
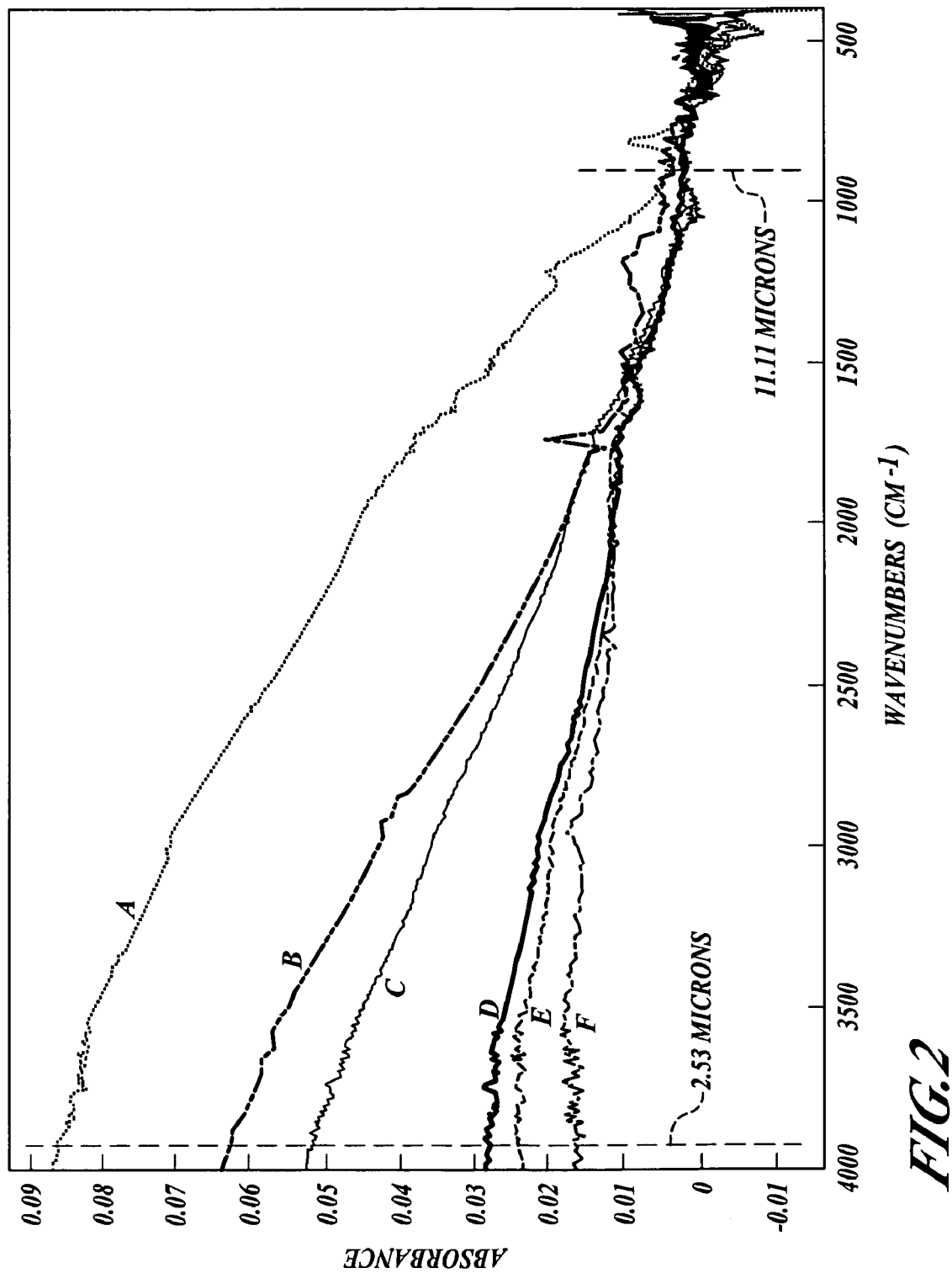
FIG. 2 is a graph of infrared absorbance of aluminum alloy polished surfaces.

FIG. 2 includes six infrared grazing angle absorbance spectra over a range of wavenumbers (cm−1) from six variously polished metallic surfaces (not shown). As is known, wavenumbers, expressed as wavelengths per centimeter (cm−1), are the inverse of wavelengths λ, expressed in centimeters. Absorbance spectra A through F show absorbance versus wavenumbers from approximately 4,000 cm−1 to approximately 400 cm−1. Absorbance in this instance is calculated as the log 10 of the quantity 1 divided by reflectivity (that is, log 10 (1/R)), and is graphed on a range of approximately −0.01 to 0.08.

Spectrum A is the absorbance spectrum of an unpolished area of an aluminum alloy surface. Spectrum A has an absorbance of approximately 0.85 at 4,000 wavenumbers and declines roughly in a straight line to 0.01 at approximately 900 wavenumbers, and then declines with variation to around 0.005 between 900 wavenumbers and 500 wavenumbers.

Spectrum B is the absorbance spectrum of a low quality polish of the same aluminum alloy surface as used for Spectrum A. Spectrum B declines in a roughly straight line from an absorbance of approximately 0.65 at 4,000 wavenumbers to approximately 0.01 at 900 wavenumbers, and then declines with variation to approximately 0.005 at 500 wavenumbers.

Spectrum C is the absorbance spectrum of a low-medium quality polish on the same aluminum alloy surface mentioned above. Spectrum C declines in a roughly straight line from an absorbance of approximately 0.53 at 4,000 wavenumbers to approximately 0.01 at 900 wavenumbers, and then declines with variation to approximately 0.005 at 500 wavenumbers.

Spectrum D is the absorbance spectrum of a good quality polish on the same aluminum alloy surface sample. Spectrum D has an absorbance of approximately 0.03 at 4,000 wavenumbers, declining in a roughly straight line to 0.01 at 900 wavenumbers, then with variation to approximately 0.005 at 500 wavenumbers.

Spectrum E is the absorbance spectrum of a very good quality polish on the same aluminum alloy surface. Spectrum E has an absorbance of approximately 0.025 at 4,000 wavenumbers declining roughly in a straight line to 0.01 at 900 wavenumbers, and then with variation to approximately 0.005 at 500 wavenumbers.

Spectrum F is the absorbance spectrum of a polished reference sample from Alcoa Company, polished to an extremely high degree. Spectrum F has an absorbance of approximately 0.018 at 4,000 wavenumbers and declines in roughly a straight line with some variability between 1,750 and 900 wavenumbers to approximately 0.01 at 900 wavenumbers, and then with variation to approximately 0.005 at 500 wavenumbers.

As shown in FIG. 2, it will be appreciated that at a wavenumber of approximately 3,900, corresponding to a wavelength of 2.53 μm, progressively higher degrees of polish exhibit decreased absorbance. At the same time, all six spectra have approximately the same absorbance at 900 wavenumbers, or a wavelength of approximately 11.11 μm. Thus, the degree of polish may suitably be correlated to absorbance at wavenumbers greater than 900, with greater differentiation exhibited at wavenumbers greater than 2,000.

It will also be appreciated that a degree of metal polish may be suitably correlated to absorbance at a single wavenumber, such as 3,900 wavenumbers. In an alternative embodiment, a degree of metal polish may suitably be correlated to a ratio between absorbance at a higher wavenumber with a lower wavenumber, utilizing absorbance at the lower wavenumber to suitably equalize, or provide a reference between the spectra of different samples. For example, aluminum alloy substrates typically exhibit absorbance of approximately 0.01 at 900 wavenumbers. However, there can be variability between samples arising from a combination of factors unrelated to the degree of surface polish such as contamination, alloy differences, and residual polishing compound. Measurement accuracy may be increased by deriving a ratio for each sample between absorbance at a higher wavenumber, suitably near 3,900 wavenumbers, to absorbance at a lower wavenumber, suitably around 900 wavenumbers. At 900 wavenumbers, variations of absorbance, where they occur, tend to arise from factors other than polish. Dividing by the absorbance at 900 wavenumbers decreases the influence of these factors on the polish measurement. In an alternate embodiment, absorbance at 900 wavenumbers may be subtracted from absorbance at the higher wavenumber, to produce a single equalized absorbance value. This alternative embodiment also decreases the influence of factors other than polish quality. Subtracting the absorbances may be preferred when absorbance at 900 wavenumbers is near or equal to zero, thus avoiding dividing by zero where a ratio of the absorbances is calculated.

In the example shown, the quality of polish for Spectrum A may be defined as a ratio of 8.5. This is the ratio between absorbance of 0.085 at 3,900 wavenumbers to 0.01 at 900 wavenumbers, indicating a poor polished quality or an unpolished area. A surface such as Spectrum E, with a very good high quality polish, has a ratio of 2.5 reflecting an absorbance of 0.025 at 3,900 wavenumbers divided by 0.01 at 900 wavenumbers. It will be appreciated that FIG. 2 is a graph of absorbance of the Spectra A–F. With absorbance being the converse of reflectivity, a comparison of reflectivity may suitably be utilized to generate results equivalent to plotting absorbance.

It will be appreciated that absorbance at wavenumbers between 2,000 and 4,000 corresponds to polish quality due to reflectance being affected by the texture of the reflected surface, in relation to the wavelength of the infrared light being reflected off that surface. Unpolished surfaces, which are rougher surfaces at a fine scale, have greater absorbance than smoother polished surfaces, especially at wavenumbers greater than 2,000.

Infrared reflectivity for bare metal at grazing angles is dependent on surface smoothness, or degree of polish, more so than the type of metal sampled. Thus, the methods of the present invention are applicable to reflectivity, and hence the degree of polish for a plurality of metals. It will be appreciated that grazing reflectivity measurement at infrared frequencies is suitably advantageous to such measurements at visual frequencies because measurements at infrared frequencies are more sensitive to surface texture at the scale present in polished metals.

Figure 3:
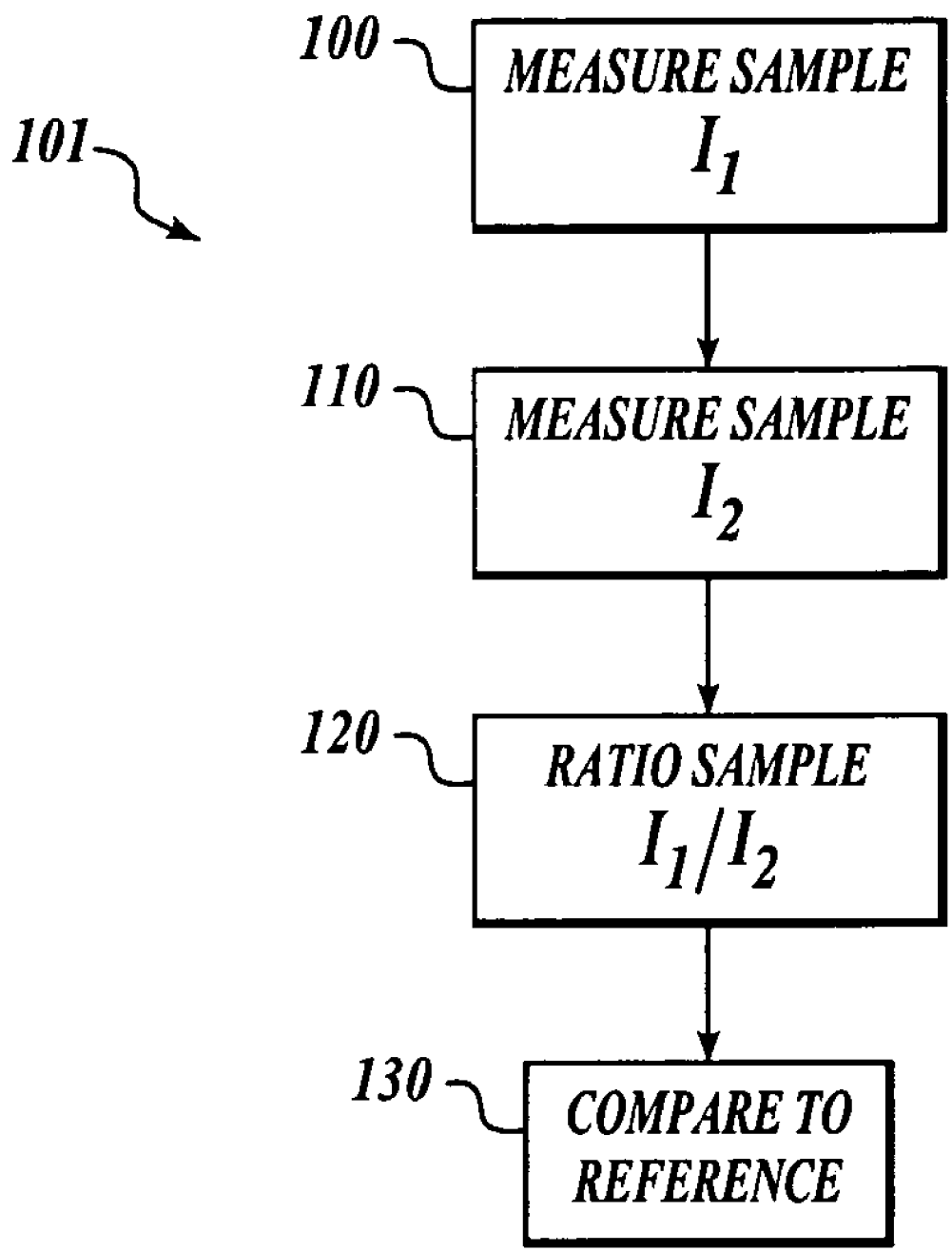
FIG. 3 is a flow chart of an exemplary testing method of the present invention.

Referring to FIG. 3, one presently preferred embodiment of the present invention is implemented through a polish measurement method 101. At a block 100, infrared reflectance $I_1$ of the sample is measured at a first frequency. At a block 110, infrared reflectance $I_2$ of the same sample at a second frequency is measured. At a block 120, a ratio is derived between $I_1$ and $I_2$. At a block 130 the ratio is compared to a reference to determine polish quality. The comparison, by way of example but not limitation, can be done manually by comparison to written reference data, or by computer.

As described above in FIGS. 2 and 3, it will be appreciated that for metal substrates, the infrared absorbance $I_1$ suitably may be obtained by measuring reflectivity at a wavenumber greater than 2,000, and suitably around 3,900. The infrared absorbance at the second frequency $I_2$ may suitably be determined at a wavenumber of around 900. In reference to FIG. 2, the method 101 of FIG. 3 produces repeatable quantitative references of polish quality. For example, an unpolished aluminum alloy surface has a ratio of approximately 8.5. A very good quality polish surface has a ratio of approximately 2.5. These ratios compare to a high quality reference with a ratio of 1.8, such as a polished aluminum alloy reference sample from Alcoa as shown in Spectrum F of FIG. 2. The method 101 of FIG. 3 thus, derives a quantitative degree of polish measurement which may be utilized for measuring the polish quality of individual samples, equipment segments, or which may be utilized during manufacture to equalize polish for adjoining or multiple sections where the degree of polish is desired to be standardized.

Figure 4:
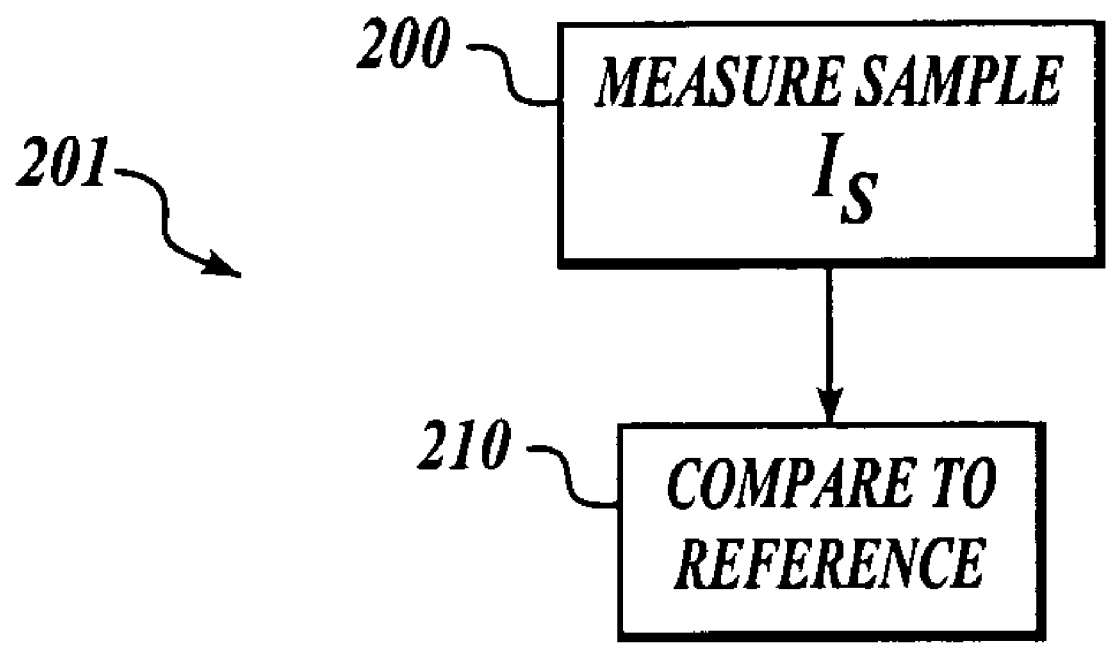
FIG. 4 is a flow chart of a further exemplary testing method of the present invention.

Referring to FIG. 4, it will be appreciated that, for samples or surfaces not significantly affected by factors other than polish quality, a measurement of infrared reflectivity at one wavenumber may be utilized to determine a degree of polish using a polish measurement method 201.

At a block 200, infrared absorbance $I_s$ of the sample is derived at a single wavenumber. At a block 210, the infrared reflectivity $I_s$ is compared to a reference surface to determine a degree of polish. Referring again to FIG. 2, the various spectra A–E of the same aluminum sample with progressively better polish quality in this sample set does not reflect variability from each other at lower wavenumbers. Thus, it has been found that absorbance at a single wavenumber greater than 2,000, and suitably around 3,900 for metals, may derive an accurate degree of polish. The method 201 does not include calculating a ratio between absorbance at a first wavenumber and absorbance at a second wavenumber. In FIG. 2, absorbance of the unpolished aluminum alloy surface at 3,900 wavenumbers of 0.085 (Spectrum A) may be directly compared with the absorbance of a very good quality polished aluminum surface at 0.025 (Spectrum E), and a highly polished reference sample from Alcoa (Spectrum F) with an absorbance of 0.018. It has been determined that equivalent levels of absorbance of polished surfaces at wavenumbers greater than 2,000, and suitably at around 3,900, correspond visually similar and equivalent polish quality. The method 201 thus, may be used to non-destructively derive a quantitative measurement of polish quality.

Figure 5:
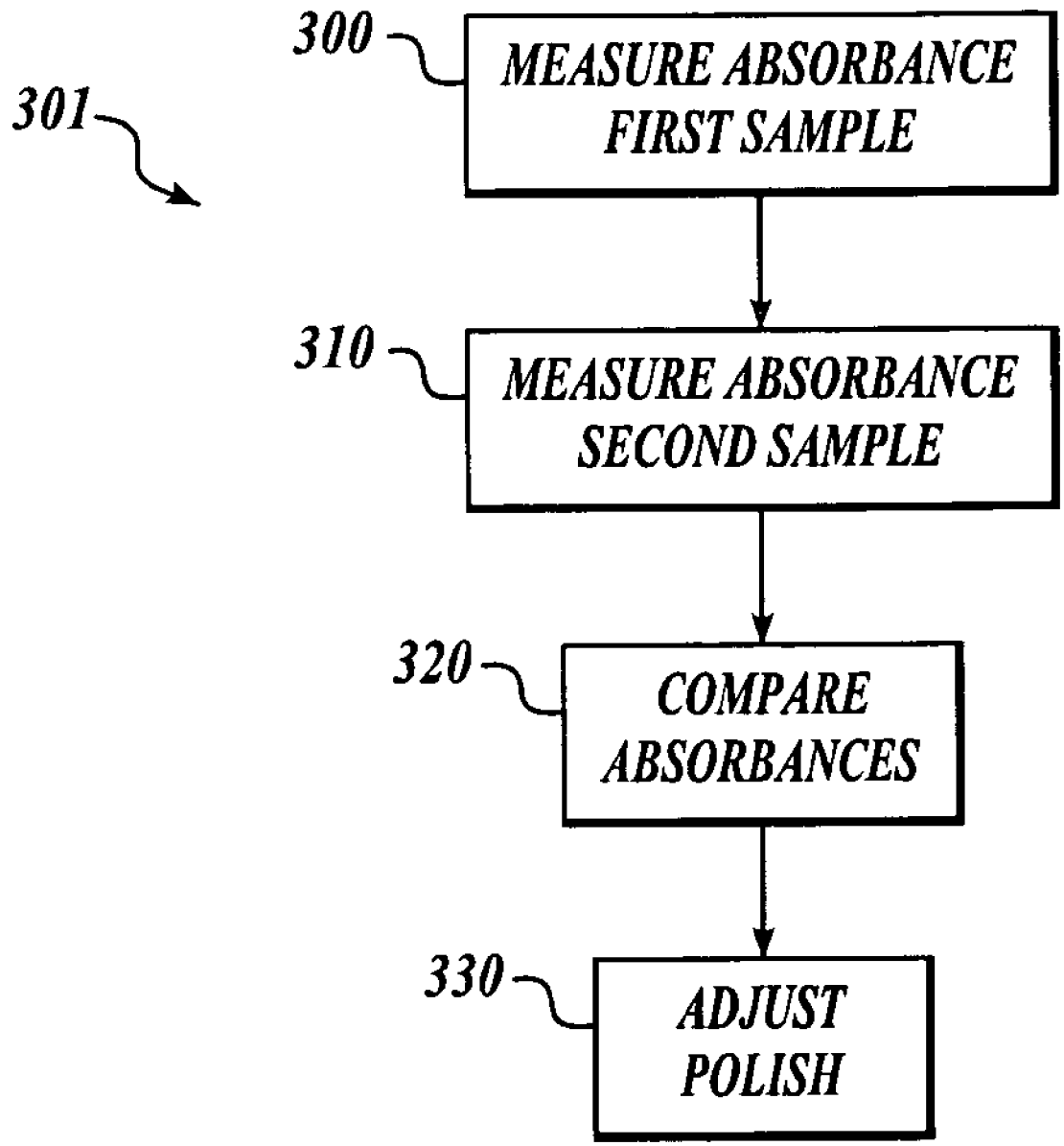
FIG. 5 is a flow chart of an exemplary polish matching method of the present invention.

It will be appreciated that a method of the present invention may be utilized to prepare uniformly polished metallic surfaces. As noted above, in an application such as aircraft involving multiple metallic panels or adjoining metallic panels, differences in polish can result in a patchworked visual appearance or different quantities of drag. In other applications where multiple independent items are desired to have the same look, whether manufactured by different parties or treated differently during their manufacturing processes, uniformity may be desired. For example, in architectural metals, a uniform look is often specified for metals being used in a building. Utilizing a method 301 of FIG. 5, standard polished surfaces may suitably be obtained.

At a block 300, the absorbance or absorbance ratio of a first sample is obtained using a method described above in connection with FIG. 3 or 4. At a block 310, the infrared absorption of a second sample is obtained using the same method as for the first sample. At a block 320 the absorbances of the two separate samples are compared. If the absorbances, and hence the degree of polish of the samples, are about equal, the method is completed. Otherwise, the polish of one or the other or both of the samples are adjusted or equalized at a block 330.

Thus, the method 301 provides equalization of polish quality of different samples. Where the polish quality of both samples is adjusted as needed, the polish quality of both samples may be standardized to yet a third sample or other reference. The method 301 of the present invention may be used to yield uniform adjoining metallic sections on equipment and uniformity among separate surfaces. It will be appreciated that for fleet vehicles, including aircraft, a common visual appearance of metallic equipment when viewed simultaneously from a variety of angles may be desired. Similarly, architectural metals used in building surfaces and trim may advantageously be equally polished. Utilizing the method 301 of FIG. 5, by way of example and not limitation, a fleet of aircraft using bare metal sections may be uniformly polished individually and across the members of the fleet. The result is a uniform appearance even when the equipment is viewed from different angles. Because the human eye picks up subtle variations in polish quality, especially at grazing angles, the method of the present invention advantageously provides a way for standardizing the visual appearance of metallic surfaces.

While the preferred embodiment of the invention has been illustrated and described, as noted above, many changes can be made without departing from the spirit and scope of the invention. Accordingly, the scope of the invention is not limited by the disclosure of the preferred embodiment. Instead the invention should be determined entirely by reference to the claims that follow.

What is claimed is:

1. A non-destructive method for determining a degree of polish of a metallic substrate, the method comprising:
    non-destructively measuring a value $I_s$ of infrared energy specularly reflected by a polished surface on a metallic substrate; and
    correlating the value $I_s$ of the infrared energy reflected to a degree of polish.

2. The method of claim 1, further comprising determining a value $I_o$ of infrared energy specularly reflected from a reference polished surface.

3. The method of claim 2, further comprising comparing $I_s$ with $I_o$.

4. The method of claim 1, wherein determining $I_s$ includes utilizing an infrared spectrometer.

5. The method of claim 4, wherein the infrared spectrometer includes an infrared imaging spectrometer.

6. The method of claim 1, wherein determining $I_s$ includes determining absorbance at at least one wavenumber corresponding with increased infrared absorbance by an unpolished metallic surface.

7. The method of claim 6, wherein the at least one wavenumber is around 3900 cm$-1$.

8. The method of claim 6, wherein correlating the infrared absorbance to a degree of polish of the sample includes deriving a ratio between the infrared absorbance of the substrate at at least two wavenumbers.

9. The method of claim 8, wherein the at least two wavenumbers are around 3900 cm$-1$ and around 900 cm$-1$.

10. The method of claim 6, wherein correlating the infrared absorbance to a degree of polish of the sample includes deriving a difference between the infrared absorbance of the sample at at least two wavenumbers.

11. The method of claim 10, wherein the at least two wavenumbers are around 3900 cm$-1$ and around 900 cm$-1$.

12. The method of claim 1, wherein the metallic substrate includes an aluminum alloy.

13. The method of claim 12, wherein determining $I_s$ includes determining absorbance at at least one wavenumber corresponding with a peak in an absorbance infrared spectrum of an unpolished aluminum surface.

14. The method of claim 13, wherein the at least one wavenumber is around 3900 cm$-1$.

15. The method of claim 1, wherein the metallic substrate includes a stainless steel alloy.

16. The method of claim 1, wherein determining a value $I_s$ of infrared energy reflected by a polished surface includes reflecting infrared energy off the polished surface at an angle of incidence less than around 45°.

17. The method of claim 1, wherein determining a value $I_s$ of infrared energy reflected by a polished surface includes reflecting infrared energy off the polished surface at an angle of incidence of around 15°.

18. The method of claim 1, wherein a degree of polish includes the smoothness of the metallic substrate.

19. A non-destructive method for determining a degree of polish on a sample, the method comprising:
   transmitting an infrared beam onto a sample of a metallic substrate;
   detecting a reflected infrared beam reflected by the sample;
   determining infrared absorbance of the sample; and
   correlating the infrared absorbance to a degree of polish of the sample.

20. The method of claim 19, wherein determining the infrared absorbance includes using an infrared spectrometer.

21. The method of claim 19, wherein correlating the infrared absorbance includes determining absorbance at at least one wavenumber corresponding with an infrared spectra of an unpolished metallic surface.

22. The method of claim 21, wherein the at least one wavenumber is around 3900 cm$-1$.

23. The method of claim 19, wherein the sample includes an aluminum alloy.

24. The method of claim 23, wherein correlating the infrared absorbance includes determining absorbance at at least one wavenumber corresponding with an infrared spectra of an unpolished aluminum surface.

25. The method of claim 24, wherein the at least one wavenumber is around 3900 cm$-1$.

26. The method of claim 24, wherein correlating the infrared absorbance to a degree of polish of the sample includes deriving a ratio between the infrared absorbance of the sample at at least two wavenumbers.

27. The method of claim 26, wherein deriving a ratio between the infrared absorbance of the sample at at least two wavenumbers includes deriving a ratio between infrared absorbance at around 3900 cm$^{-1}$ and at around 900 cm$^{-1}$.

28. The method of claim 19, wherein transmitting an infrared beam onto a sample includes transmitting the infrared beam at an angle of incidence less than around 45°.

29. The method of claim 19, wherein transmitting an infrared beam onto a sample includes transmitting the infrared beam at an angle of incidence of around 15°.

30. A non-destructive method for determining a degree of polish of a sample, the method comprising:
   transmitting an infrared beam onto a sample of a metallic substrate;
   detecting a reflected infrared beam reflected by the sample;
   determining a first infrared absorbance of the sample from the reflected infrared beam at a first wavenumber;
   determining a second infrared absorbance of the sample from the reflected infrared beam at a second wavenumber;
   deriving a first ratio between the first infrared absorbance and the second infrared absorbance; and
   quantitatively determining a degree of polish by correlating the first ratio to a reference sample.

31. The method of claim 30, wherein correlating the first ratio to a reference sample includes comparing the first ratio with a second ratio of infrared absorbance at the first wavenumber and the second wavenumber for the reference sample.

32. The method of claim 30, wherein determining at least one of the first infrared absorbance and the second infrared absorbance includes using an infrared spectrometer.

33. The method of claim 30, wherein correlating the infrared absorbance includes determining absorbance at at least one wavenumber corresponding with an infrared spectra of an unpolished surface.

34. The method of claim 30, wherein the sample includes an aluminum alloy.

35. The method of claim 34, wherein the first wavenumber is around 3900 cm$-1$.

36. The method of claim 34, wherein the second wavenumber is around 900 cm$-1$.

37. The method of claim 30, wherein transmitting an infrared beam onto a sample includes transmitting the infrared beam at an angle of incidence less than around 45°.

38. The method of claim 30, wherein transmitting an infrared beam onto a sample includes transmitting the infrared beam at an angle of incidence of around 15°.

39. A non-destructive method for determining a degree of polish of an aluminum alloy surface, the method comprising:
   transmitting an infrared beam onto an aluminum alloy surface;
   detecting a reflected infrared beam reflected by the surface;
   determining a first infrared absorbance of the surface at a wavenumber of around 3900 cm$-1$; and
   correlating the first infrared absorbance to a degree of polish of the aluminum surface.

40. The method of claim 39, wherein an infrared spectrometer determines the infrared absorbance.

41. The method of claim 39, further comprising determining a second infrared absorbance of the surface at a wavenumber of around 900 cm−1.

42. The method of claim 41, further comprising deriving a ratio between the first infrared absorbance and the second infrared absorbance.

43. The method of claim 41, further comprising subtracting the second infrared absorbance from the first infrared absorbance.

44. The method of claim 39, wherein transmitting an infrared beam onto the aluminum alloy surface includes transmitting the infrared beam at an angle of incidence less than around 45°.

45. The method of claim 39, wherein transmitting an infrared beam onto the aluminum alloy surface includes transmitting the infrared beam at an angle of incidence of around 15°.

46. A non-destructive method for standardizing a degree of polish of metallic surfaces, the method comprising:
  transmitting an infrared beam onto a first metallic surface;
  detecting a reflected infrared beam reflected by the first metallic surface;
  determining a first infrared absorbance of the first metallic surface;
  transmitting an infrared beam onto a second metallic surface;
  detecting a reflected infrared beam reflected by the second metallic surface;
  determining a second infrared absorbance of the second metallic surface; and
  comparing the first infrared absorbance to the second infrared absorbance.

47. The method of claim 46, further comprising changing the degree of polish of at least one of the first metallic surface and the second metallic surface.

48. The method of claim 46, further comprising equalizing the first infrared absorbance towards about the second infrared absorbance.

49. The method of claim 46, wherein the first metallic surface and the second metallic surface include an aluminum alloy.

50. The method of claim 49, wherein the first metallic surface and the second metallic surface form at least part of an exterior surface of a vehicle.

51. The method of claim 50, wherein the vehicle includes an aircraft.

52. The method of claim 49, further comprising determining a second infrared absorbance of the surface at a wavenumber of around 900 cm−1.

53. The method of claim 52, further comprising deriving a ratio between the first infrared absorbance and the second infrared absorbance.

54. The method of claim 46, wherein transmitting an infrared beam onto the aluminum alloy surface includes transmitting the infrared beam at an angle of incidence less than around 45°.

55. The method of claim 46, wherein transmitting an infrared beam onto the aluminum alloy surface includes transmitting the infrared beam at an angle of incidence of around 15°.

56. The method of claim 46 wherein the first metallic surface and the second metallic surface form at least part of a building.

* * * * *